United States Patent

Ladner et al.

Patent Number: 5,928,912
Date of Patent: *Jul. 27, 1999

[54] PROCESS FOR THE HYDROXYLATION OF AROMATIC ACIDS USING STRAINS OF THE FUNGUS BEAUVERIA

[75] Inventors: Wolfgang Ladner, Fussgoenheim; Horst Ralf Staudenmaier, Limburgerhof; Bernhard Hauer; Ursula Mueller, both of Fussgoenheim; Uwe Pressler, Altrip; Joachim Meyer, Maxdorf; Hardo Siegel, Speyer, all of Germany

[73] Assignee: BASF Aktiengesellschaft, Ludwigshafen, Germany

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/566,589

[22] Filed: Dec. 4, 1995

Related U.S. Application Data

[62] Continuation-in-part of application No. 08/410,205, Mar. 24, 1995, abandoned, which is a continuation-in-part of application No. 08/256,020, filed as application No. PCT/EP92/02891, Dec. 14, 1992, abandoned.

[30] Foreign Application Priority Data

Dec. 24, 1991 [DE] Germany ............................... 41 42 943

[51] Int. Cl.⁶ .................................................... C12P 7/42
[52] U.S. Cl. ......................... 435/146; 435/132; 435/911
[58] Field of Search .................................... 435/132, 146, 435/911

[56] References Cited

FOREIGN PATENT DOCUMENTS 11362  10/1990  European Pat. Off. .

OTHER PUBLICATIONS

J.A. Von Arx, *The Genera of Fungi Sporulatin in Pure Culture*, p. 310, 1981.
*Advances in Penicillium and Aspergillus Syst matics*, Samson et al., 1985, p. 31.
Fungal Metabolism III, S.M. Bocks, Phytochemistry Bd. 6, Nr. 6, 1967, New York, U.S.
Kieslich, K, "Microbial Transformations of Non–Steroid Cyclic Compounds", 1976, J. Wiley, pp. 107–108.
Yoshizako, et al., *Agric. Biol. Chem.*, 49(3) pp. 877–879, 1985.
Sugumaran, et al., J. Indian Inst. Sci., 1979, 60(8), pp. 125–141.
Holland, H. L. "Organic Synthesis with Oxidative Enzymes" 1992, pp. 72–74.
ATCC Catalogue of Fungi, 1991 pp. 74–76.

*Primary Examiner*—Irene Marx
*Attorney, Agent, or Firm*—Keil & Weinkauf

[57] ABSTRACT

A process for hydroxylating compounds of the formula

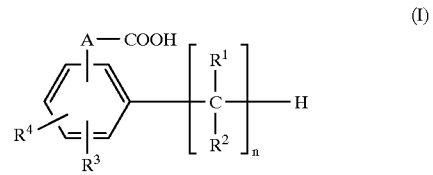

(I)

where n, A and $R^1$ to $R^4$ have the meanings stated in the description, with the aid of microorganisms of the genus Beauveria.

2 Claims, No Drawings

PROCESS FOR THE HYDROXYLATION OF AROMATIC ACIDS USING STRAINS OF THE FUNGUS BEAUVERIA

This application is a continuation-in-part of application Ser. No. 08/410,205, filed on Mar. 24, 1995, which is a continuation-in-part of application Ser. No. 08/256,020, filed on Jun. 21, 1994, both now abandoned, which is a national stage of PCT/EP 92/02891 filed Dec. 14, 1992.

The present invention relates to a process for hydroxylating with the aid of microorganisms.

It is known that microorganisms are able to hydroxylate aromatic compounds. This usually results in dihydroxylated compounds or mixtures of various regioisomers (Biochem J. 65 (1957) 682). It is also known that 2-phenoxypropionic acid can be oxidized regioselectively to 2-(4-hydroxyphenoxy)propionic acid (WO 90/11362).

We have found a process for hydroxylating compounds of the formula I

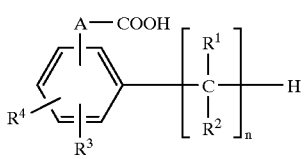

where n is 0 or 1,

A is a bond, $C_1$–$C_4$-alkylene or $C_1$–$C_4$-alkyleneoxy, $R^1$ is hydrogen, $C_1$–$C_8$-alkyl, $C_1$–$C_4$-alkoxy or $C_1$–$C_4$-alkylthio, $R^2$ is hydrogen or $C_1$–$C_8$-alkyl which is unsubstituted or substituted by a halogen or a $C_1$–$C_4$-alkoxy, $R^3$ is halogen, $C_1$–$C_4$-alkyl, $C_1$–$C_4$-alkoxy, nitro, cyano, carbamoyl or $C_1$–$C_4$-alkoxycarbonyl, and phenoxy or naphthoxy which is unsubstituted or substituted by 1 or 2 halogens, hydroxyl, $C_1$–$C_4$-alkyl or $C_1$–$C_4$-alkoxy groups, and $R^4$ is hydrogen, halogen, $C_1$–$C_4$-alkyl or $C_1$–$C_4$-alkoxy or the salts thereof, which comprises hydroxylating the compounds of the formula I or the salts thereof under aerobic conditions in the presence of a fungus.

The process is particularly suitable for hydroxylating compounds of a formula I where n is 0 or 1, $R^1$ is methyl, ethyl or isopropyl, $R^2$ is hydrogen or methyl, $R^3$ is halogen (especially fluorine, chlorine or bromine), methyl, methoxy, ethoxy or phenoxy, and $R^4$ is hydrogen, halogen (especially fluorine, chlorine or bromine) or methyl.

A large number of fungi are suitable for the process. Fungi which can be used can be isolated, for example, from soil samples, especially humus-containing soil samples. Particularly suitable for the conversion are Aspergillus and Beauveria strains as well as Streptomyces. Also suitable are fungi of the genus Rhizoctonia. These fungi can be obtained, for example, from collections of strains. Their suitability for the hydroxylation can be established in a simple preliminary test. The strains *Beauveria bassiana, Aspergillus niger,* Aspergillus spec., *Streptomyces hygroscopicus* and Streptomyces spec. have proven particularly suitable.

To carry out the process according to the invention, suitable strains are inoculated on a nutrient medium containing the compound I and incubated aerobically therein under conditions favorable to growth and production by the particular microorganism. The fermentation is carried out continuously or batchwise for from 1 to 10 days.

The cells of the microorganism, which can also be used in the form of resting, non-growing cells, are allowed to act directly on the substrate. It is possible to use any known incubation processes, but particular preference is given to fermenters in the form of deep, aerated and agitated tanks. Very good results are obtained by incubation of a liquid nutrient medium.

Suitable nutrient media contain sources of carbon and nitrogen, and inorganic salts, with or without small amounts of trace elements and vitamins. Sources of nitrogen which can be used are inorganic or organic nitrogen compounds or materials which contain these compounds. Examples are ammonium salts, nitrates, corn steep liquor, brewer's yeast autolyeate, soybean meal, wheat gluten, yeast extract, yeast, urea and potato protein. Examples of carbon sources which can be used are sugars such as glucose, polyols such as glycerol or fats such as soybean oil.

Examples of inorganic salts are the salts of calcium, magnesium, manganese, potassium, zinc, copper, iron and other metals. The phosphate ion is particularly suitable as anion of the salts. Growth factors may be added to the nutrient medium, such as, for example, biotin, riboflavin or other vitamins.

The ratios of the said nutrients in the mixture depends on the type of fermentation and is determined in each individual case.

The concentrations of compound I generally suitable for carrying out the process according to the invention are from about 1 to 100 g/l, preferably from about 5 to 50 g/l.

The cultivation conditions are fixed so as to achieve the best possible yields. Cultivation is preferably carried out at from 20° C. to 40° C., particularly advantageously from 25° C. to 30° C. The pH is preferably kept in the range from 3 to 9, particularly advantageously from 4 to 7. An incubation time of from 15 to 100 hours is generally sufficient. The maximum quantity of the required product accumulates in the medium during this time. The acid is preferably added in the form of a salt, eg. the sodium salt. The acid can be added to the nutrient medium all at once at the start, after growth has taken place or during the cultivation in a plurality of portions or continuously.

It is preferable to use the compound I as the free acid, but it is also possible to employ its salts. Preferred salts are alkali metal and alkaline earth metal salts, for example the Na, K and Li salts.

The novel process is suitable for the oxidation both of racemic compounds I and of their antipodes. The center of asymmetry is usually unaffected by the process according to the invention. The novel process thus represents a straightforward and low-cost way of selectively preparing hydroxy derivatives of the compounds I.

The following rules apply to the introduction of the hydroxyl group into the compound I.

Hydroxylation of an aromatic ring results in the oxygen in position 4.

The more electron-rich of two aromatic rings is hydroxylated.

If the aromatic compound has an oxidizable side chain it is possible in principle for hydroxylation of the nucleus and oxidation of the side chain to take place. The preferred oxidation depends on the nature of the side chain (eg. steric hindrance) and on the position on the aromatic compound:

Hydroxylation of the nucleus preferred for position 2,

Oxidation of the side chain preferred for position 3

Exclusively oxidation of the side chain for position 4.

A 2-methyl is about 35% oxidized.

A 2-ethyl is not oxidized.

Sterically demanding groups such as isopropyl undergo terminal oxidation which is very predominantly enantioselective. The absolute configuration of the new center of chirality is as yet unknown.

The corresponding alcohols are always the products of oxidation of the side chain.

If there is more than one oxidizable side group, there is always oxidation of only one group to the alcohol, particularly preferentially the side chain at position 4. If there is no substituent at this position, the group in position 3 or 5 is oxidized.

The hydroxylated compounds I are valuable intermediates for preparing crop protection agents (U.S. Pat. No. 4,750,931) and pharmaceutical substances.

The following Examples illustrate the invention:

EXAMPLE

The following nutrient media were used:

medium A 50 g/l glucose 10 g/l yeast extract 0.5 g/l magnesium sulfate 7-hydrate 1.5 g/l potassium dihydrogen phosphate 3.6 g/l dipotassium hydrogen phosphate 3 g/l Carbopol® 946 (carboxyvinylpolymer with extremely high-molecular weight)

2 µg/l iron(II) sulfate 1-hydrate

10 µg/l zinc(II) sulfate 4-hydrate

300 µg/l boric acid

200 µg/l cobalt(II) chloride 6-hydrate

10 µg/l copper(II) chloride 2-hydrate

20 µg/l nickel(II) chloride 6-hydrate

30 µg/l sodium molybdate 2-hydrate

The pH was adjusted to 6.8 with 5 N sodium hydroxide solution. Glucose and phosphates were each autoclaved separately at 121° C. for 10 minutes. The (R)-2-phenoxypropionic acid was dissolved in water with a little 5 N sodium hydroxide solution and sterilized by filtration. The remaining medium was autoclaved at 121° C. for 10 minutes.

100 ml portions of the sterile medium were introduced into sterile 500 ml Erlenmeyer flasks, which were provided with a sterile cotton plug. A loop of spores of the fungus strain *Beauveria bassiana* ATCC 7159 was inoculated into one flask. *Beauveria bassiana* ATCC 7159 is deposited at the American Type Culture Collection, 10801 University Boulevard, Manassas, Va. 20110-2209, USA. The flask was then incubated at 28° C., shaking at 250 rpm, for three days. Three of these culture broths were in each case used as preculture for a fermentation on the 10 l scale.

A fermenter containing 10 l of sterile medium (composition as above) and 10 g/l of the compounds listed in Table 1 as Na salt solution sterilized by filtration was inoculated with 300 ml of the preculture obtained as above. Fermentation was carried out at from 28 to 29° C. stirring at from 400 to 600 rpm and with an aeration rate of from 0.5 to 1.5 vvm. Where necessary during the fermentation, sterile glucose solution (50% w/v) was added in amounts of up to 50 g/l. The progress of the conversion was followed by gas chromatography. To do this, 1000 µl of fermentation broth were removed and mixed with 100 µl of concentrated hydrochloric acid and 800 µl of ethyl acetate and thoroughly mixed for 15 s. 700 µl of the organic phase were cautiously removed and evaporated in the sample tube at 50° C. under a gentle stream of nitrogen. The residue was dissolved in 70 µl of ethyl acetate and transferred quantitatively into a sample tube for gas chromatography. To this were added 30 µl of N-methyl-N-trimethylsilyltrifluoroacetamide. The sample was then investigated by gas chromatography.

After the fermentation was complete, concentrated sulfuric acid was added to pH 2 and the products were isolated by extraction with methyl t-butyl ether, drying with $Na_2SO_4$, evaporation, and, if necessary, crystallization. The products were identified by $^1$H-NMR and $^{13}$C-NMR spectroscopy. The results are compiled in the Table.

The yields ranged from 60 to 95%.

TABLE

| No. | Starting material | Product | Fermentation time (days) |
|---|---|---|---|
| 1 | 2-(2-chlorophenoxy)propionic acid | 2-(2-chloro-4-hydroxyphenoxy)propionic acid | 14 |
| 2 | 2-(3-chlorophenoxy)propionic acid | 2-(3-chloro-4-hydroxyphenoxy)propionic acid | 6 |
| 3 | 2-(2-fluorophenoxy)propionic acid | 2-(2-fluoro-4-hydroxyphenoxy)propionic acid | 4 |
| 4 | 2-(3-fluorophenoxy)propionic acid | 2-(3-fluoro-4-hydroxyphenoxy)propionic acid | 5 |
| 5 | 2-(2-ethylphenoxy)propionic acid | 2-(2-ethyl-4-hydroxyphenoxy)propionic acid | 3 |
| 6 | 2-(2-isopropoxyphenoxy)propionic acid | 2-(2-isopropoxy-4-hydroxyphenoxy)propionic acid | 10 |
| 7 | 2-(2-methylphenoxy)propionic acid | a) 2-(2-methyl-4-hydroxyphenoxy)propionic acid<br>b) 2-(2-hydroxymethylphenoxy)propionic acid | 5 |
| 8 | 2-(3-methylphenoxy)propionic acid | a) 2-(3-methyl-4-hydroxyphenoxy)propionic acid<br>b) 2-(3-hydroxymethylphenoxy)propionic acid | 3 |
| 9 | 2-phenoxybenzoic acid | 2-(4-hydroxyphenoxy)benzoic acid | 7 |
| 10 | 2-(4-methylphenoxy)propionic acid | 2-(4-hydroxymethylphenoxy)propionic acid | <2 |
| 11 | 2-(2,3-dimethylphenoxy)propionic acid | 2-(3-hydroxymethyl-2-methylphenoxy)propionic acid | 2.5 |
| 12 | 2-(2,4-dimethylphenoxy)propionic acid | 2-(4-hydroxymethyl-2-methylphenoxy)propionic acid | <2 |
| 13 | 2-(2,5-dimethylphenoxy)propionic acid | 2-(5-hydroxymethyl-2-methylphenoxy)propionic acid | 2.5 |
| 14 | 2-(3,4-dimethylphenoxy)propionic acid | a) 2-(4-hydroxymethyl-3-methylphenoxy)-propionic acid<br>b) 2-(3-hydroxymethyl-4-methylphenoxy)- | <2 |

TABLE-continued

| | | | |
|---|---|---|---|
| 15 | 2-(3,5-dimethylphenoxy)propionic acid | propionic acid 2-(3-hydroxymethyl-5-methylphenoxy)-propionic acid | 2.5 |
| 16 | 2-(2,3,4-trimethylphenoxy)propionic acid | 2-(4-hydroxymethyl-2,3-dimethylphenoxy)-propionic acid | 5 |
| 17 | 2-(2,3,5-trimethylphenoxy)propionic acid | 2-(5-hydroxymethyl-2,3-dimethylphenoxy)-propionic acid | 6 |
| 18 | 2-(2,3,6-trimethylphenoxy)propionic acid | 2-(3-hydroxymethyl-2,6-dimethylphenoxy)-propionic acid | 5 |
| 19 | 2-(2,4,5-trimethylphenoxy)propionic acid | 2-(4-hydroxymethyl-2,5-dimethylphenoxy)-propionic acid | 4 |
| 20 | 2-(2,4,6'-trimethylphenoxy)propionic acid | 2-(4-hydroxymethyl-2,6-dimethylphenoxy)-propionic acid | 5 |
| 21 | 2-(3,4,5-trimethylphenoxy)propionic acid | 2-(3-hydroxymethyl-4,5-dimethylphenoxy)-propionic acid | 6 |
| 22 | 2-(3-ethylphenoxy)propionic acid | 2-[3-(1-hydroxyethyl)phenoxy]propionic acid[1) | 3 |
| 23 | 2-(4-ethylphenoxy)propionic acid | 2-[4-(1-hydroxyethyl)phenoxy]propionic acid[1) | 5 |
| 24 | 2-(4-n-propylphenoxy)propionic acid[1) | 2-[4-(1-hydroxypropyl)phenoxy]propionic | 4 |
| 25 | 2-(4-n-butylphenoxy)propionic acid | 2-[4-(1-hydroxybutyl)phenoxy]propionic acid[1) | 4 |
| 26 | 4-methylphenylacetic acid | 4-hydroxylmethylphenylacetic acid | 7 |
| 27 | 3-methylphenylacetic acid | 3-hydroxymethylphenylacetic acid | 7 |
| 28 | (R)-2-(4-isopropylphenoxy)propionic acid | (R)-2-[4-(1-hydroxymethylethyl)phenoxy]-propionic acid[2) | 4 |

[1)]The center of chirality which is formed is virtually racemic.
[2)]The oxidation results very predominantly in one enantiomer.

We claim:

1. A process for hydroxylating a compound of the formula I

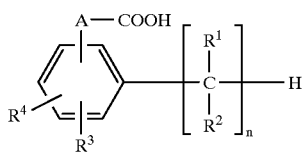

(I)

wherein, n is 0 or 1;

A is —$CH_2$— or —$OCH(CH_3)$—

$R^1$ is selected from the group consisting of hydrogen, $C_1$–$C_8$-alkyl, $C_1$–$C_4$-alkoxy and $C_1$–$C_4$-alkylthio;

$R^2$ is selected from the group consisting of hydrogen, unsubstituted $C_1$–$C_8$-alkyl, halogen-substituted $C_1$–$C_8$-alkyl and $C_1$–$C_4$-alkoxy-substituted $C_1$–$C_8$-alkyl;

$R^3$ is selected form the group consisting of halogen, $C_1$–$C_4$-alkyl, $C_1$–$C_4$-alkoxy, nitro, cyano, carbamoyl, $C_1$–$C_4$-alkoxycarbonyl, phenoxy and naphthoxy; said naphthoxy radical being unsubstituted or substituted by one or two halogens, or by a radical selected from the group consisting of hydroxyl, $C_1$–$C_4$-alkyl and $C_1$–$C_4$-alkoxy;

$R^4$ is selected from the group consisting of hydrogen, halogen, $C_1$–$C_4$-alkyl and $C_1$–$C_4$-alkoxy; or the salts thereof;

said hydroxylation taking place at the 4-position relative to the acidic substituent or at the side-chain substituents or both substituents;

which process comprises cultivating a fungus of the genus Beauveria under aerobic conditions in the presence of a compound of formula I until the hydroxylated compound is produced; and then recovering the hydroxylated compound.

2. The process of claim 1, wherein the fungus is *Beauveria bassiana* ATCC 7159.

* * * * *

UNITED STATES PATENT AND TRADEMARK OFFICE
CERTIFICATE OF CORRECTION

PATENT NO.: 5,928,912

DATED: July 27, 1999

INVENTOR(S): LADNER etal.

It is certified that error appears in the above-identified patent and that said Letters Patent is hereby corrected as shown below:

Col. 6, claim 1, line 28, "form" should be --from--.

Signed and Sealed this

Twenty-first Day of December, 1999

Attest:

Q. TODD DICKINSON

*Attesting Officer*   *Acting Commissioner of Patents and Trademarks*